United States Patent [19]

Grace et al.

[11] Patent Number: 5,263,952
[45] Date of Patent: Nov. 23, 1993

[54] TWO-PIECE TIP FOR FIBER OPTIC CATHETER

[75] Inventors: Kenneth P. Grace, Woodland Park; Roland W. Songer; Dan J. Hammersmark, both of Colorado Springs, all of Colo.

[73] Assignee: Spectranetics, Colorado Springs, Colo.

[21] Appl. No.: 857,485

[22] Filed: Mar. 25, 1992

[51] Int. Cl.⁵ .............................................. A61B 17/36
[52] U.S. Cl. ......................................... 606/15; 606/7; 606/16; 607/93
[58] Field of Search ............... 606/3, 7, 9, 10–17; 128/395–398, 4, 6

[56] References Cited

U.S. PATENT DOCUMENTS

| | | |
|---|---|---|
| 3,780,740 | 12/1973 | Rhea . |
| 4,368,730 | 1/1983 | Sharrock . |
| 4,519,390 | 5/1985 | Horne ................... 606/15 |
| 4,592,353 | 6/1986 | Daikuzono ............ 606/16 |
| 4,768,858 | 9/1988 | Hussein . |
| 4,769,014 | 9/1988 | Russo . |
| 4,769,016 | 9/1988 | Labianca . |
| 4,817,613 | 4/1989 | Jaraczewski et al. . |
| 4,848,339 | 7/1989 | Rink et al. ............. 606/7 |
| 4,850,351 | 7/1989 | Herman et al. ......... 606/7 |
| 4,860,743 | 8/1989 | Abela . |
| 4,863,424 | 9/1989 | Blake et al. . |
| 4,863,442 | 9/1989 | DeMello et al. . |
| 4,967,745 | 11/1990 | Hayes et al. . |
| 4,968,306 | 11/1990 | Huss et al. . |
| 4,968,314 | 11/1990 | Michaels . |
| 4,993,412 | 2/1991 | Murphy-Chutorian . |
| 5,032,123 | 7/1991 | Katz et al. . |
| 5,034,010 | 7/1989 | Kittrell et al. . |
| 5,041,108 | 8/1991 | Fox et al. . |
| 5,041,109 | 8/1991 | Abela . |

*Primary Examiner*—Peter A. Aschenbrenner
*Attorney, Agent, or Firm*—Cushman, Darby & Cushman

[57] ABSTRACT

A device for terminating a surgical apparatus such as a fiber optic catheter is disclosed. A fiber optic catheter having an outer body, an inner body disposed within the outer body to form an outer lumen therebetween and an inner lumen within the inner body, and optical fibers within the outer lumen is terminated at its distal end with a two-piece tip. An outer band of the tip has one end between the outer body and the optical fibers, while an inner band contacts the ends of the inner body and the optical fibers. The terminal faces of the optical fibers may be angled to increase the surface area illuminated or ablated by the fiber optic catheter. The inner and outer bands may be flared outwardly to increase the surface area affected even more. The inner body may also be extended beyond the terminal face to aid tracking of the catheter. The inner body and inner band may be eccentric to the outer body and outer band so that the catheter may be rotated to ablate a larger vascular area.

72 Claims, 3 Drawing Sheets

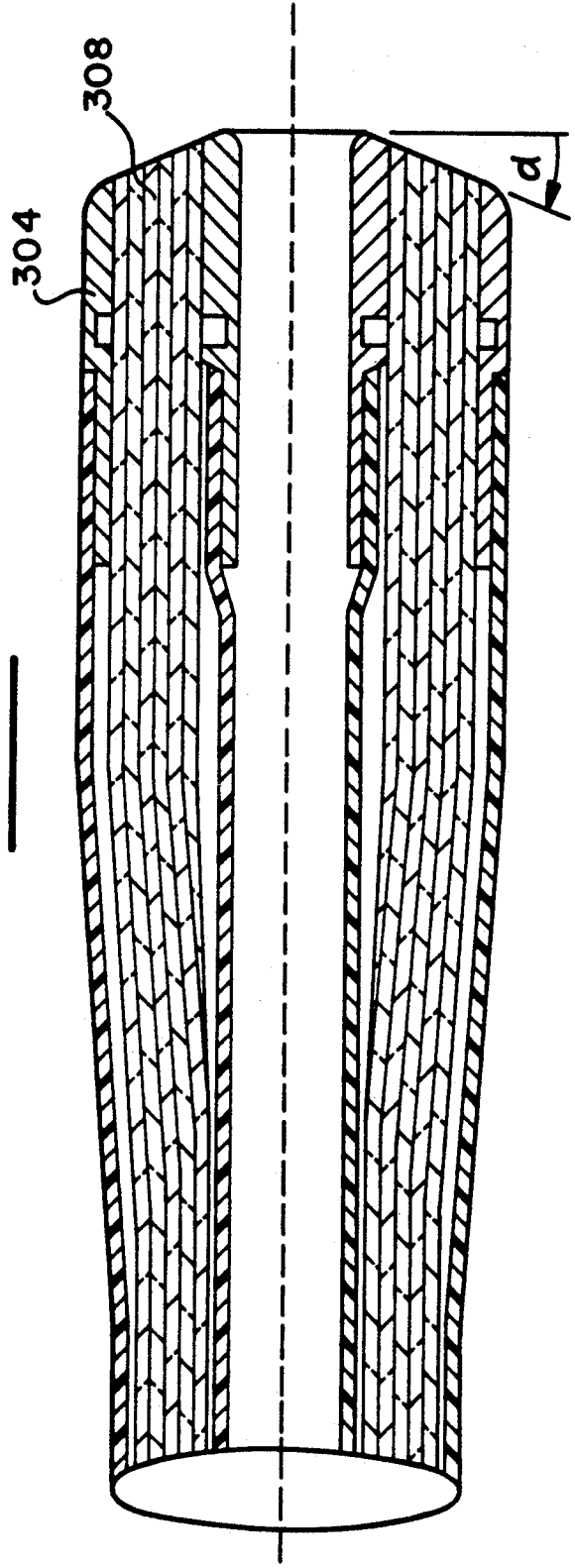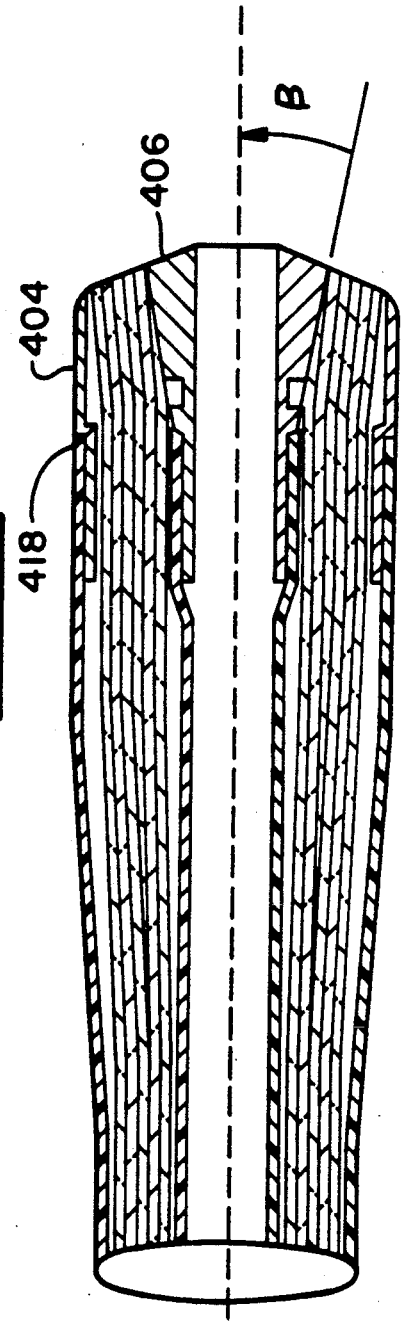

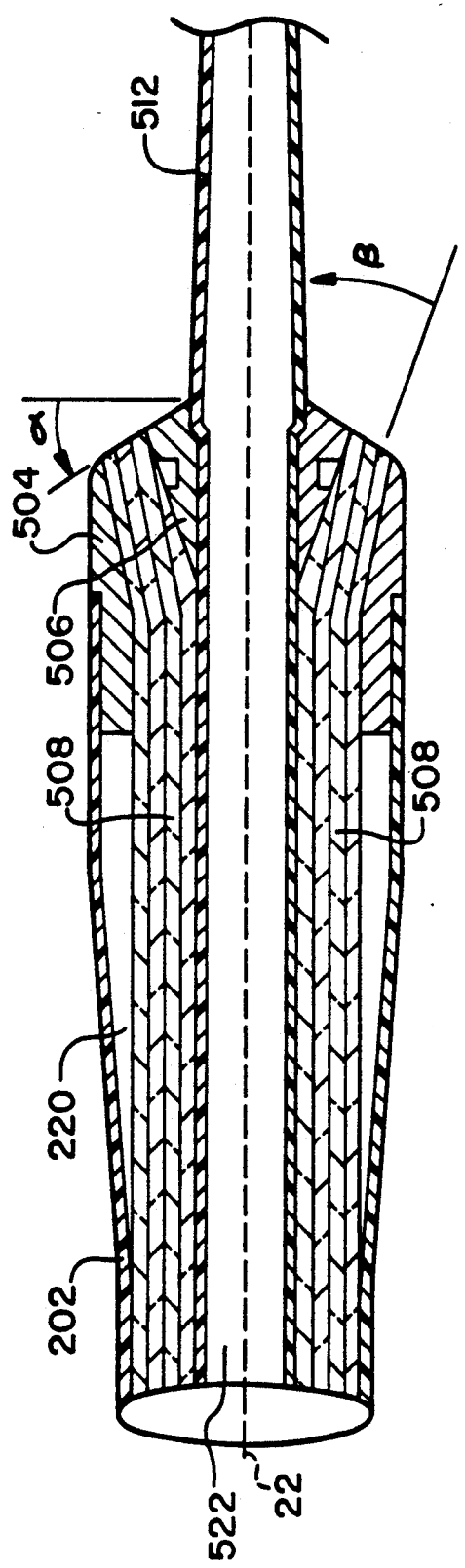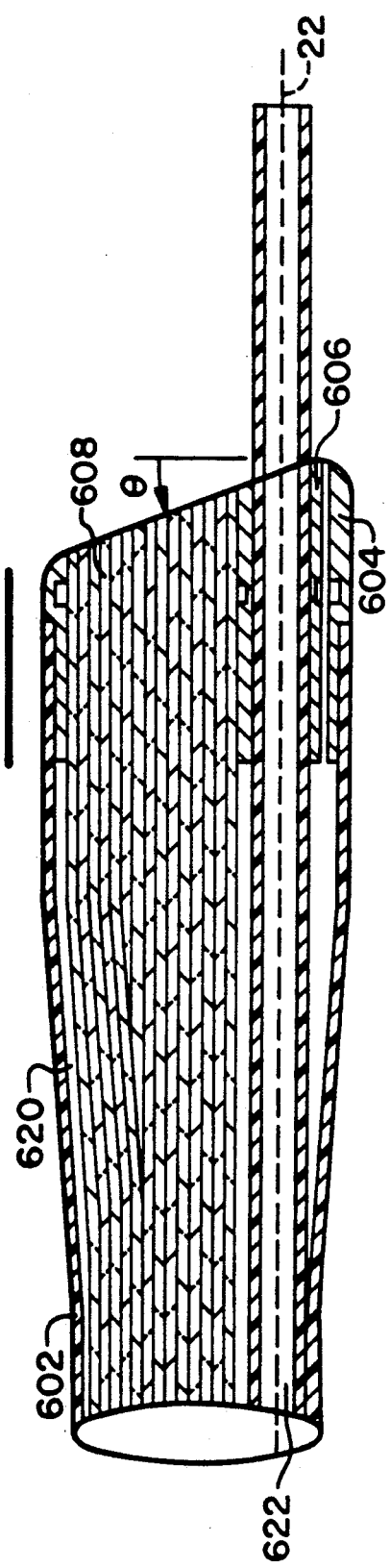

TWO-PIECE TIP FOR FIBER OPTIC CATHETER

BACKGROUND OF THE INVENTION

1. Field of the Invention

The present invention relates to catheters used for surgical operations, and more specifically, to fiber optic catheters used for illuminating and ablating intravascular regions and means for terminating such catheters.

2. Description of the Related Art

Fiber optic catheters have been constructed in which hollow tubular devices, or catheters, containing optical fibers, are inserted into veins or arteries. Radiant energy is conducted along the fibers to illuminate internal parts of the body for diagnostic and surgical purposes. There are many medical applications in which it is desirable to deliver energy, such as laser energy, through an optical fiber or similar waveguide device disposed in a body cavity for treatment or diagnosis. These include the ablation of tissue such as plaque and tumors, the destruction of calculi and the heating of bleeding vessels for coagulation. The lasers used may produce either pulsed or continuous-wave light of wavelengths ranging from the ultra-violet to the infra-red.

Fiber optic catheters have been employed to generate heat at the distal end of the catheter as the mechanism of operation. One known system employs laser radiation for heating a metal tip on the end of the fiber so that the heated tip burns through the plaque obstructing the vessel. This is disadvantageous in that the tip may burn through the wall of the vessel. Moreover, the location and degree of burning cannot be precisely controlled using this type of tip, and tissue from the vessel wall may stick to the hot tip. As a result, the tissue tears as the tip is moved, producing a thrombosis. The heated metal tip also requires mechanical pressure to force the tip through the plaque, and is not very successful with blockages located at any substantial distance from the entry point of the catheter, or in small winding cardiac arteries, since sufficient mechanical pressure cannot be exerted on the tip to force it through the plaque.

In another proposed solution a sapphire tip, through which energy passes to the surrounding tissue, has been used. The surface of a highly polished sapphire is difficult to bond to a glass fiber, and accordingly secure junctions between optical fibers and sapphire cannot be produced. For this reason the sapphire is mounted on a metal connector fixed to a catheter through which the fiber is passed. Such a device is thick and relatively inflexible, making it unsuitable for use in small blood vessels or where it is required to pass a balloon catheter over it. Also, it is difficult to maintain the position of the fiber with respect to the sapphire, and the junction becomes contaminated with charred blood. Since the refractive index of sapphire is higher than that of the fiber, there is a heat loss at the sapphire-fiber interface and the metal tip becomes heated, thus introducing the disadvantages mentioned above.

U.S. Pat. No. 4,860,743 and U.S. Pat. No. 5,041,109 to Abela disclose a tip for a laser catheter based on a combination of the metal tip/sapphire lens concepts where sapphire spherical lenses on the tip are used to deliver some laser energy directly to an area being ablated, while some of the energy is used to heat the metal tip. In this way, plaque blocking the vessel is vaporized to allow the catheter to be moved farther into the vessel, while the remaining obstructive tissue is burned away.

Ball-tipped or lens-tipped devices have been proposed, and these can be readily formed merely by melting the tip of a silica-glass optical fiber. There are, however, problems with respect to the mechanical strength and safety for such tips, particularly after exposure to heat, laser light and the mechanical stresses of clinical uses. A supporting structure, for example a metal collar, can be employed with such tips, but this arrangement becomes heated in use, again with the disadvantages mentioned above.

U.S. Pat. No. 4,967,745 to Hayes et al., U.S. Pat. No. 5,032,123 to Katz et al., and U.S. Pat. No. 5,034,010 to Kittrell et al. disclose laser catheters having a transparent shield over the distal end of the optical fibers. A similar design is disclosed in U.S. Pat. No. 5,041,108 to Fox et al., which uses individual lenses for each optical fiber to focus the laser beam onto the area to be illuminated.

All of the above fiber optic catheter tips are disadvantageous in that they require great effort and care to fabricate. For instance, in many cases, the tips must be machined with individual channels for the optical fibers. In such a case, the channels must be precision machined to ensure their concentric placement about the catheter tip for even light distribution. Also, the relatively complex shapes of the above-mentioned tips do not allow for the precise machining of the tip surfaces at desired angles and dimensions.

After the tip is fabricated, a great deal of effort is required to properly assemble the individual components into a device that will withstand normal field use and perform as expected. For instance, it is desirable to glue the tip onto the laser catheter to secure it for normal field use. In this case, it is difficult to accurately control the wicking action of the glue along the optical fibers when using one of the aforementioned tips.

SUMMARY OF THE INVENTION

It is an object of this invention to provide a tip for a catheter that can be easily and cheaply fabricated.

It is a further object of this invention to provide a catheter tip that provides for illumination of a greater area than catheter tips presently known in the art.

It is a further object of this invention to provide a tip for a catheter that can easily be assembled.

The above objects are achieved by providing a two-tip for a fiber catheter having an outer body and an inner body disposed within the outer body to form an outer lumen therebetween and an inner lumen disposed within the inner body. Optical fibers are disposed within the outer lumen. The tip according to the present invention comprises an inner band that is placed radially inward of the optical fibers at the distal end of the inner body. An outer band is similarly situated on the outside of the optical fiber ring. In this manner, the optical fibers are "clamped" into place between the inner and outer bands. The catheter tip may be held together by potting using epoxy. The catheter tip may then be polished to provide a smooth surface for delivering energy. The ends of the optical fibers may have exit surfaces which are perpendicular to the axis of the catheter. Alternatively, the ends of the optical fibers may have exit surfaces at an angle from the perpendicular to present a more rounded, less traumatic profile for passage through vascular channels.

The tip may be constructed so that the ends of the optical fibers do not extend parallel to the catheter axis. One possibility is to construct an inner band and an outer band having a conical shape instead of a cylindrical shape. In this way, the fibers are flared outwardly at the distal end of the catheter, thus providing a less traumatic catheter tip profile and providing an increased radial component to the emitted energy, enlarging the area over which energy is radiated.

Additionally, the inner body may extend beyond the end of the optical fibers and the remainder of the catheter. The extended inner body provides an element of intermediate stiffness between a guide wire passing through the catheter and the catheter itself. This feature improves the ability of the catheter to track the guide wire and causes the catheter to align coaxially with the target during ablation.

BRIEF DESCRIPTION OF THE DRAWINGS

These and other objects and advantages of this invention will become apparent and more readily appreciated from the following description of the presently preferred exemplary embodiments, taken in conjunction with the accompanying drawings, of which:

FIG. 3 is a cross-sectional view of a second embodiment of a catheter tip according to the present invention;

FIG. 4 is a cross-sectional view of a variation of the second embodiment of a catheter tip according to the present invention;

FIG. 5 is a cross-sectional view of a third embodiment of a catheter tip according to the present invention; and FIG. 6 is a cross-sectional view of a fourth embodiment of a catheter tip according to the present invention.

DETAILED DESCRIPTION OF THE PRESENTLY PREFERRED EXEMPLARY EMBODIMENTS

Figure 1:
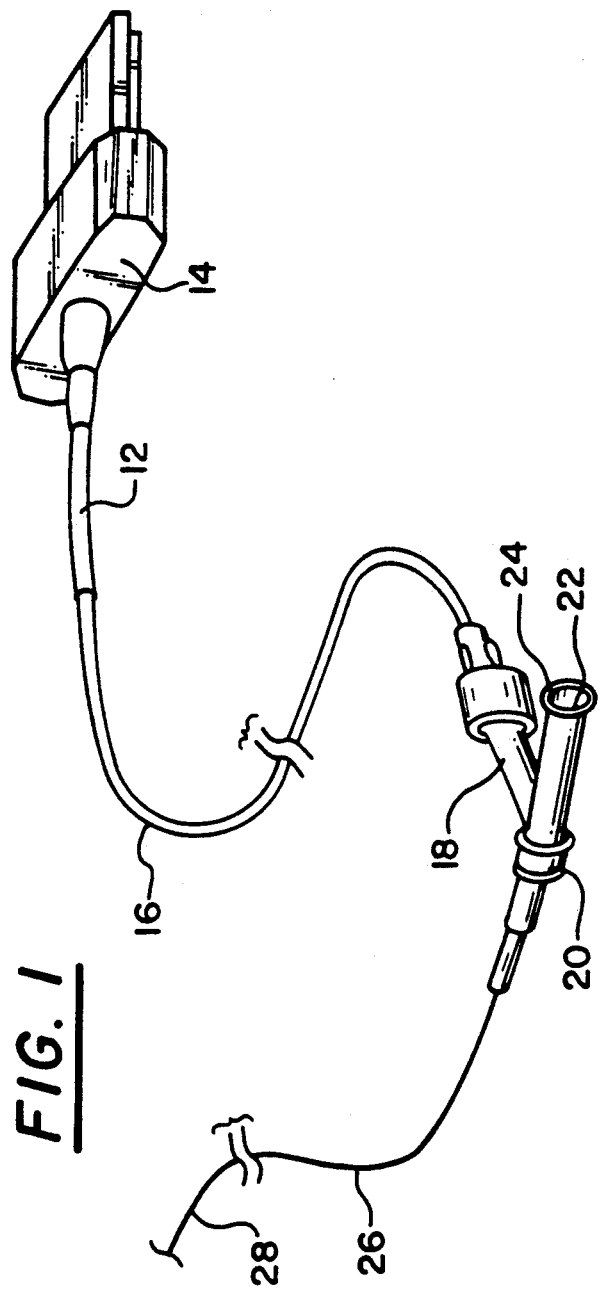
FIG. 1 is a perspective view of a fiber optic catheter and associated tip according to the present invention.

FIG. 1 depicts a perspective view of a fiber optic catheter 10 according to the present invention. A proximal end 12 of a light conveying cable 16 is connected to a proximal mount 14. The light conveying cable 16 has optical fibers disposed within, and these fibers are affixed to the proximal mount 14 using techniques known in the art. A second end of the light conveying cable 16 is attached to a side branch 18 of a bifurcating adaptor 20, and a guide wire 22 is fed into the inline branch 24 of the bifurcating adaptor 20. The other end of the bifurcating adaptor 20 is attached to a, catheter 26, which has an outer body, an inner body disposed within the outer body to form an outer lumen therebetween and an inner lumen disposed within the inner body, optical fibers disposed within the lumen, and guide wire 22 running through the inner of catheter 26. The inner body and outer body may be constructed from any of a number of suitable materials, such as plasticized vinyl resins, polyethylene, synthetic and natural rubbers and polyurethane elastomers. The distal end of catheter 26 is terminated by tip 28, which will be described more fully herein.

Figure 2:
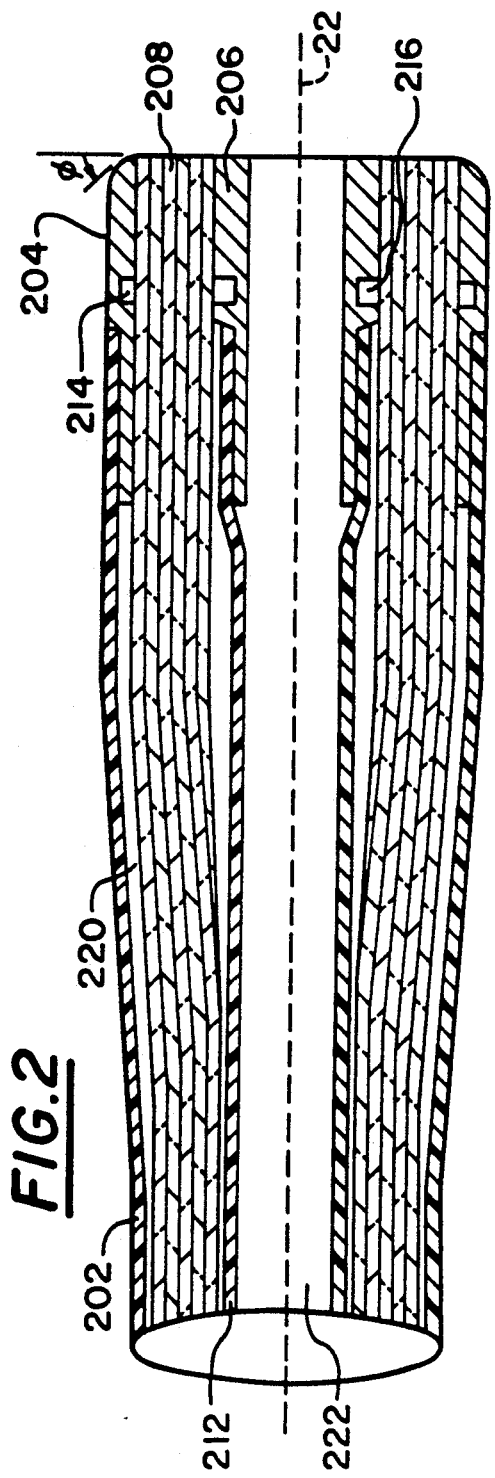
FIG. 2 is an enlarged cross-sectional view of a catheter tip according to a first embodiment of the present invention.

FIG. 2 is a cross-sectional view of one embodiment of the catheter tip of FIG. 1. The internal structure of the catheter tip according to the present invention is clearly illustrated in this drawing. Outer body 202 and inner body 212 are disposed about a common central axis substantially coincident with guide wire 22, and optical fibers 208 are disposed throughout to form an outer lumen 220 therebetween and an inner lumen 222 within inner body 212. Outer band 204 has a proximal end t is inserted between the distal end of the outer body 202 and the optical fibers 208 and is bonded to the outer body 202. A distal end of the outer band 204 extends to approximately the same position as the distal end of the optical fibers 208. A proximal end of inner band 206 covers and is bonded to an interior surface of a distal end of inner body 212. Glue is forced among optical fibers 208 to form a glue plug, bonding fibers 208 to inner band 206 and outer band 204.

To ensure that the outer band 204 is secured in place, outer band 204 has an intermediate portion having an increased inner diameter, thus forming notch 214. This notch cooperates with the glue plug formed in the optical fibers 208 to prevent the outer band 204 from being pulled apart from the rest of the catheter. Similarly, the inner band 206 is provided with notch 216 that cooperates with the glue plug formed in the optical fibers 208, thus securing the inner band 206 in place. Alternatively, outer band 204 may be countersunk on its distal end, thereby forming a shoulder which cooperates with the glue plug in a similar manner. This arrangement is depicted by shoulder 418 in FIG. 4.

The exterior surface of the proximal end of the outer band 204 and the exterior surface of the proximal end of the inner band 206 may be sandblasted to provide a suitable surface for bonding to the outer body and the inner body, respectively. The components may be bonded using, for instance, a cyanoacrylate adhesive.

As described above, a proximal end of inner band 106 may cover an interior surface of a distal end of inner body 212. Alternatively, the distal end of inner body 212 may extend along the interior surface of inner band 206 and extend to be substantially coterminal with, or even extend beyond, the distal end of inner band 206, as depicted in FIG. 5.

As shown in FIG. 2, the distal rim of the outer band 204 may be beveled at an angle $\phi$ to give the catheter tip a less traumatic profile, thus enabling the tip to pass through vascular channels more easily. A bevel angle $\phi$ of sixty degrees from the face of the tip has been found to provide good results. Also, a small area of the terminal face of the optic fiber bundle 208 may also be beveled to provide a smooth transitional area. Similarly, the rim of inner band 206 may be beveled at a like angle to avoid forming a sharp corner that could traumatize vascular tissue.

The inner band 206 and the outer band 204 are preferably constructed of a radiopaque material such as platinum. Such construction allows the exact position and orientation of the tip to be detected via fluoroscopic analysis and displayed to an operating physician.

FIG. 3 depicts a cross-sectional view of a second embodiment of the present invention. This embodiment is similar to the first embodiment and can have the same variations as described with respect to the first embodiment. The major distinction between this and the first embodiment is that the terminal ends of the optical fibers 308 may be polished at an angle $\alpha$ with respect to a plane perpendicular to a longitudinal axis of the catheter. Generally, larger values of o provide less traumatic profiles for the catheter tip; however, $\alpha$ must be limited to approximately 25° or less to avoid massive internal reflection from the polished face of the fiber, thus inducing catastrophic light transmission failure in the fiber. Generally, a value of $\alpha$ in the range of 18° to 23° has been found to provide an acceptable tip profile while avoiding massive internal reflection.

An added advantage of polishing the terminal end of the optical fibers 308 at a positive angle $\alpha$ is that rim dead space may be decreased. In other words, to provide a non-traumatic profile on a catheter tip having optical fibers with a perpendicular face polish, the outer band must be relatively thick to allow a sufficiently rounded corner to be machined into it. On the other hand, the radius that must be machined on outer band 304 is much less due to the angle of the fiber ends, and the outer band 304 may therefore be thinner, thus providing a smaller catheter tip diameter.

FIG. 4 depicts a variation on the above embodiment where inner band 406 is tapered so that its outer diameter gradually increases toward its distal end. A taper angle of 2°–4° has proven effective in forcing concentricity of the optical fibers and in compensating for fiber diameter tolerances. As noted above, FIG. 4 also shows outer band 404 having a shoulder 418 instead of a notch as in the previous embodiments.

Furthermore, the taper of inner band 406 and the shoulder of outer band 404 causes the ends of the optical fibers not to extend parallel to the catheter axis. In this way, the fibers are flared outwardly at the distal end of the catheter, thus providing a less traumatic catheter tip profile and providing an increased radial component to the emitted energy, enlarging the area over which energy is radiated.

FIG. 5 depicts a third embodiment of a catheter tip according to the present invention which implements this concept. A portion of inner body 512 is disposed within outer body to form an outer lumen 220 therebetween and an inner lumen 222 disposed within inner body 512 body 202, and optical fibers 508 are disposed throughout outer lumens 520. Outer band 504 has a proximal end that is inserted between the distal end of the outer body 202 and the optical fibers 508 and is bonded to the outer body 512. A distal end of the outer band 504 t extends as far as the distal end of the optical fibers 508.

In this embodiment, inner body 512 does not cover the proximal end of inner band 506; instead, it covers the interior surface of inner band 506 as illustrated in FIG. 5. Inner body 512 may be substantially coterminal with the distal end of inner band 506, or it may extend beyond the distal end of inner band 506. This extended inner lumen portion provides an element of intermediate stiffness between the relatively flexible guide wire 22 and the relatively rigid catheter tip. This transitional stiffness zone or "strain relief" increases the ability of the catheter to follow a path defined by the guide wire 22 and the ability of the catheter to align coaxially with a target during ablation.

The stiffness of the extended inner body may be augmented with a coil, laminate or a similar element. A coil made of metal or some other radiopaque material is particularly advantageous in providing an operator with information on the catheter tip position.

If inner body 512 extends beyond the distal end of inner band 506, the distal rim of inner band 506 may be beveled or countersunk to fit an enlarged portion of inner body 512, as shown in FIG. 5. This feature advantageously seats inner body 512 in inner band 506, thus providing added structural integrity to the catheter tip.

The radially inner surface of outer band 504 and the radially outer surface of inner band 506 are angled with respect to the central axis of the catheter so that the terminal ends of the optical fibers 508 are bent at an angle $\beta$ with respect to the axis of the catheter. Such an angle allows the catheter to assume a smoother profile to reduce the potential for traumatization of vascular tissue. Generally, greater values of $\beta$ provide less traumatic profiles; however, the angle at which the fibers may be bent without damage is limited as a function of their radii. In one embodiment of the invention, $0° \leq \beta \leq 25°$.

Flaring the fibers radially outward increases the radial component of the energy emitted by the fibers. As a result, energy is emitted over a larger area.

The terminal ends of the optical fibers may be polished substantially perpendicular to their longitudinal axes in a manner similar to the first embodiment of this invention, or they may be polished at a positive angle to a plane perpendicular to their longitudinal axes. This additional angle is limited to approximately 25° (and, advantageously, should be between 18° and 23°) to avoid catastrophic failure of the fibers' light transmitting properties. In this way, the total angle of the terminal surfaces of optical fibers 508 is $\alpha$ from a plane perpendicular to a longitudinal axis of the catheter. Thus, the angle of the terminal surfaces can be 40° or more, thus increasing the angle of termination and providing an less traumatic profile.

In this embodiment, a notch 516 is provided on inner band 506 at the band-fiber interface similar to those previously discussed in order to secure the inner band 506 to the rest of the catheter assembly. It has been found that the flared structure of the tip enables outer band 504 to be fixed on the catheter assembly without similar provisions.

The embodiments illustrated in FIGS. 2-5 all have inner lumens concentric with the outer bodies. Alternatively, the inner bodies may be eccentric from the outer bodies. FIG. 6 depicts an example of such an eccentric embodiment. In this embodiment, inner band 606 and inner body 612 and inner lumen 622 are eccentric to outer band 604, and outer body 602 and outer lumen 620; that is, they are arranged so that they do not share a common longitudinal axis.

This eccentric design is advantageous because the catheter may be rotated about the guide wire 22 in inner lumen 622, thereby causing the optical fibers 608 to be moved in a circular fashion. This causes a larger vascular region to be impacted by the light energy from the fibers.

In this embodiment, the distal end of the catheter presents a substantially planar face. The face of the catheter may be perpendicular to its longitudinal axis in a manner similar to FIG. 2. Alternatively, the catheter face may be at a positive angle $\Theta$ to a plane perpendicular to the longitudinal axis of the catheter as shown in FIG. 6. This design aids proper tracking of the catheter tip. As above, the angle $\Theta$ is limited to approximately 25° or less to avoid massive internal reflection from the polished face of the fiber, thus inducing catastrophic light transmission failure in the fiber.

The angled face is advantageous in that it provides a self-aligning feature, particularly with respect to eccentric obstructions in a vessel. If an obstruction lies to one side of a vessel, the distal-most part of the tip will align with the side of the vessel not obstructed so that the optical fibers are brought in contact with the obstruction.

A method of making the present invention will now be described with particular reference to FIG. 2. First, the outer band 204 and the inner band 206 are machined from a suitable material. As was discussed above, this material may be platinum or some other radiopaque, relatively non-reactive material. Next, the inner body 212 is bonded to the inner band 206 using suitable adhesive such as cyanoacrylate. As has been discussed the portion of inner band 206 contacting inner body 212 may be sandblasted to provide a rough surface for adhesion.

Once the inner band 206 is affixed to the inner body 212, the optical fibers 208 are formed around the assembly and assembly is pulled into the outer body 202. Then, outer band 204 is slid into position on the assembly. Alternatively, the entire assembly may be retracted so that it is positioned properly with respect to the outer band 204.

Then, the outer body is retracted from the remaining assembly to expose the distal ends of the fibers. The glue plug is now formed around the optical fibers 208. Epoxy is wicked up the optical fibers 208 from the distal end of the catheter to form a glue plug in the fibers 208 in the area between the inner band 206 and the outer band 204. As described above, the glue plug helps to secure the tip assembly to the catheter.

Outer band 204 is repositioned and bonded to outer body 202. As described above, the portion of the outer band 204 contacting the outer body 202 may be sandblasted to provide a better adhesive surface. By this process, a tip for a fiber optic catheter according to the present invention can be fabricated.

Although a few preferred embodiments of the invention have been shown and described, it will be appreciated by those skilled in the art that changes may be made in these embodiments without departing from the principles and the spirit of the invention, the scope of which is defined in the appended claims.

What is claimed is:

1. A tip for terminating a distal end of a catheter, said catheter having an outer body, an inner body disposed within said outer body to form an outer lumen therebetween and an inner lumen disposed within said inner body, and a plurality of optical fibers disposed within said outer lumen, said tip comprising:
   an outer band constructed to permit a proximal end of said outer band to contact and be bonded to a distal end of said outer body; and
   an inner band constructed so that said inner band may be disposed substantially within said outer band and also constructed to permit a proximal end of said inner band to contact and be bonded to said inner body, said inner band being separate from said outer band to allow light energy to exit from a distal end of said catheter.

2. The tip of claim 1, wherein a portion of said outer band has an enlarged inner diameter on a distal portion thereof defining a shoulder between said enlarged inner diameter portion and the remainder of said outer band.

3. The tip of claim 1, wherein said outer band has an intermediate portion having an increased inner diameter.

4. The tip of claim 1, wherein said inner band has an intermediate portion having a reduced outer diameter.

5. The tip of claim 1, wherein at leas tone of said outer band interior surface and said inner band exterior surface is at a positive angle $\beta$ with respect to a longitudinal axis of said catheter.

6. The tip of claim 1, wherein said outer band is beveled on a distal rim thereof at a non-zero angle $\phi$ from a plane perpendicular to a longitudinal axis of said catheter.

7. The tip of claim 6, wherein $\phi \approx 60°$.

8. The tip of claim 1, wherein at least one of said inner band and said outer band is made of a radiopaque material.

9. The tip of claim 8, wherein said radiopaque material is platinum.

10. The tip of claim 1, wherein said inner band and said outer band are eccentric.

11. A catheter having an outer lumen, and an inner lumen disposed within said outer lumen, said catheter comprising:
    light energy conveying means for conveying light energy to a target area separate from said catheter, said light energy conveying means including a plurality of optical fibers disposed between said inner lumen and said outer lumen; and
    a tip including an outer band radially outward from said optical fibers and an inner band radially inward from said optical fibers to enable light exiting said optical fibers to exit a distal end of said catheter from between said inner band and said outer band.

12. The catheter of claim 11, wherein said outer band has a proximal end contacting and bonded to said outer body.

13. The catheter of claim 12, wherein a portion of said proximal end of said outer band has a reduced outer diameter and said outer band contacts and bonds to said outer body at said reduced outer diameter portion.

14. The catheter of claim 11, wherein said outer band has an enlarged inner diameter on a distal portion thereof defining a shoulder between said enlarged inner diameter portion and the remainder of said outer band.

15. The catheter of claim 14, further comprising a glue plug disposed proximate to said shoulder for affixing said outer band to said catheter.

16. The catheter of claim 11, wherein said outer band has an intermediate portion having an increased inner diameter.

17. The catheter of claim 16, further comprising a glue plug disposed proximate to said increased inner diameter portion for affixing said outer band to said catheter.

18. The catheter of claim 11, wherein said inner band further comprises a proximal end contacting and bonded to an interior surface of said inner body on an exterior surface of said inner band.

19. The catheter of claim 11, wherein a portion of said proximal end of said inner band has a reduced outer diameter and said inner band contacts and bonds to said inner body at said reduced outer diameter portion.

20. The catheter of claim 11, wherein said inner band has an intermediate portion having a reduced outer diameter.

21. The catheter of claim 20, further comprising a glue plug disposed proximate to said reduced outer diameter portion for affixing said inner band to said catheter.

22. The catheter of claim 11, further comprising a glue plug disposed between said outer band and said inner band for fixing the position of said optical fibers.

23. The catheter of claim 11, said optical fibers further comprising a terminal surface, said terminal surface being on an exterior surface of said catheter, said terminal surface having a non-zero angle $\alpha$ with respect to a plane perpendicular to a longitudinal axis of said catheter.

24. The catheter of claim 23, wherein $\alpha \leq 25°$.

25. The catheter of claim 11, wherein
the distal ends of said optical fibers are angled away from a longitudinal axis of said catheter at an angle $\beta$.

26. The catheter of claim 25, said optical fibers further comprising a terminal surface, said terminal surface being on an exterior surface of said catheter, said terminal surface having a non-zero angle $\alpha$ with respect to a plane perpendicular to a longitudinal axis of said catheter.

27. The catheter of claim 26, wherein $\alpha \leq 45°$.

28. The catheter of claim 11, wherein at least one of said outer band and an outer portion of a terminal surface of said optical fibers is beveled on an edge thereof at an angle $\phi$.

29. The catheter of claim 28, wherein $\phi \approx 60°$.

30. The catheter of claim 11, wherein at least one of said inner band and said outer band is made of a radiopaque material.

31. The catheter of claim 30, wherein said radiopaque material is platinum.

32. The catheter of claim 11, wherein an exterior surface of at least one of a proximal end of said outer band and a proximal end of said inner band is sandblasted.

33. The catheter of claim 11, wherein said tip is potted using a potting substance.

34. The catheter of claim 33, wherein said potting substance is a rigid polishable epoxy.

35. The catheter of claim 11, wherein said inner band and said outer band are eccentric.

36. A catheter having an outer lumen, an inner lumen disposed within said outer lumen, and a plurality of optical fibers disposed therebetween, a distal end of said catheter being terminated at a tip, said tip comprising:
an outer band radially outward from said optical fibers;
wherein a portion of a distal end of said inner body extends beyond a distal end of said outer band.

37. The catheter of claim 36, wherein said outer band has a proximal end contacting and bonded to said outer body.

38. The catheter of claim 36, wherein a portion of said outer band has an enlarged inner diameter on a distal portion thereof defining a shoulder between said enlarged inner diameter portion and the remainder of said outer band.

39. The catheter of claim 38, further comprising a glue plug disposed proximate to said shoulder for affixing said outer band to said catheter.

40. The catheter of claim 36, wherein said outer band has an intermediate portion having an increased inner diameter.

41. The catheter of claim 40, further comprising a glue plug disposed proximate to said increased inner diameter portion for affixing said outer band to said catheter.

42. The catheter of claim 36, further comprising:
an inner band radially inward from said optical fibers.

43. The catheter of claim 42, wherein said inner band further comprises a proximal end contacting and bonded to an interior surface of said inner lumen on an exterior surface of said inner band.

44. The catheter of claim 42, wherein said proximal end of said inner band has a reduced outer diameter and said inner band contacts and bonds to said inner lumen at said reduced outer diameter portion.

45. The catheter of claim 42, wherein a portion of said inner band has an intermediate portion having a reduced outer diameter.

46. The catheter of claim 45, further comprising a glue plug disposed proximate to said reduced outer diameter portion for affixing said inner band to said catheter.

47. The catheter of claim 42, further comprising a glue plug disposed between said outer band and said inner band for fixing the position of said optical fibers.

48. The catheter of claim 42, wherein
said inner band is beveled on a distal rim thereof to form a beveled surface, and
said inner body comprises a portion an increased outer diameter, said increased outer diameter portion contacting said inner band at said beveled surface.

49. The catheter of claim 42, said optical fibers further comprising a terminal surface, said terminal surface being on an exterior surface of said catheter, said terminal surface having a non-zero angle $\alpha$ with respect to a plane perpendicular to a longitudinal axis of said catheter.

50. The catheter of claim 49, wherein $\alpha \leq 25°$.

51. The catheter of claim 42, wherein
at least one of said outer band interior surface and said inner band exterior surface is at a non-zero angle $\beta$ with respect to a longitudinal axis of said catheter.

52. The catheter of claim 51, at least one of said outer band and said inner band further comprising a terminal surface, said terminal surface having a non-zero angle $\alpha$ with respect to a plane perpendicular to a longitudinal axis of said catheter.

53. The catheter of claim 52, wherein $\alpha \leq 45°$.

54. The catheter of claim 42, wherein at least one of said outer band and an outer portion of a terminal surface of said optical fibers is beveled on an edge thereof at an angle $\phi$.

55. The catheter of claim 54, wherein $\phi \approx 60°$.

56. The catheter of claim 42, wherein at least one of said inner band and said outer band is made of a radiopaque material.

57. The catheter of claim 56, wherein said radiopaque material is platinum.

58. The catheter of claim 42, wherein an exterior surface of at least one of a proximal end of said outer band and a proximal end of said inner band is sandblasted.

59. The catheter of claim 36, wherein said tip is potted using a potting substance.

60. The catheter of claim 36, wherein said potting substance is a rigid polishable epoxy.

61. The catheter of claim 36, wherein said inner band and said outer band are eccentric.

62. The catheter of claim 61, wherein an exterior surface of said inner band contacts an interior surface of said outer band.

63. The catheter of claim 61, wherein a distal end of said fibers lie in a plane intersecting a plane perpendicular to a longitudinal axis of said catheter at a non-zero angle Θ.

64. The catheter of claim 63, wherein Θ≦25°.

65. The catheter of claim 63, wherein said inner body extends from a distal-most portion of said catheter.

66. The catheter of claim 42, wherein said portion of said distal end of said inner body extending beyond said distal end of said inner band comprises:
  a strain relief disposed in said extended inner body portion.

67. The catheter of claim 66, wherein said strain relief is a radiopaque coil.

68. A catheter comprising:
  an outer body;
  an inner body extending within said outer body; and
  a plurality of optical fibers disposed between said outer body and said inner body;
  wherein a distal end of said inner body extends beyond a distal end of at least one of said outer body and said optical fibers; and
  said distal end of said inner body is less stiff than a portion of said catheter adjacent said distal end of said outer body.

69. The catheter of claim 68, said plurality of optical fibers comprising a terminal surface, said terminal surface having a non-zero angle with respect to a longitudinal axis of said catheter.

70. The catheter of claim 68, wherein a terminal portion of said optical fibers is beveled on an edge thereof at an angle.

71. The catheter of claim 68, wherein said inner body and said outer body are eccentric.

72. The catheter of claim 71, wherein a distal end of said optical fibers lie in a plane intersecting a plane perpendicular to a longitudinal axis of said catheter at a non-zero angle.

* * * * *

UNITED STATES PATENT AND TRADEMARK OFFICE
CERTIFICATE OF CORRECTION

PATENT NO. : 5,263,952
DATED : November 23, 1993
INVENTOR(S) : GRACE ET AL

It is certified that error appears in the above-indentified patent and that said Letters Patent is hereby corrected as shown below:

On the title page, Item [75] Inventors:, second inventor's first name reads: "Roland" should read --Ronald--.

On the title page, Item [21]: Appl. No. : Reads: "857,485" should read --857,458

Signed and Sealed this

Thirty-first Day of May, 1994

Attest:

BRUCE LEHMAN

*Attesting Officer*     Commissioner of Patents and Trademarks